(12) United States Patent
Markin

(10) Patent No.: US 8,812,241 B1
(45) Date of Patent: Aug. 19, 2014

(54) METHOD FOR NORMALIZING CLINICAL LABORATORY MEASUREMENTS

(75) Inventor: Rodney S. Markin, Omaha, NE (US)

(73) Assignee: Prairie Ventures, L.L.C., Omaha, NE (US)

( * ) Notice: Subject to any disclaimer, the term of this patent is extended or adjusted under 35 U.S.C. 154(b) by 501 days.

(21) Appl. No.: 12/914,603

(22) Filed: Oct. 28, 2010

Related U.S. Application Data

(60) Provisional application No. 61/255,979, filed on Oct. 29, 2009.

(51) Int. Cl.
*G01N 33/50* (2006.01)

(52) U.S. Cl.
USPC .............. 702/19; 702/179; 435/6.14; 435/7.1

(58) Field of Classification Search
USPC ..................... 702/19, 179; 435/6.12, 6.14, 7.1
See application file for complete search history.

(56) References Cited

U.S. PATENT DOCUMENTS

| | | | |
|---|---|---|---|
| 6,204,066 B1 * | 3/2001 | Wardlaw ......................... | 436/70 |
| 2008/0154099 A1 * | 6/2008 | Aspel et al. .................... | 600/301 |

OTHER PUBLICATIONS

Angelo Tinazzi, From Local Laboratory to Standardisation and beyond Applying a common grading system, PhUSE, 2007.*

* cited by examiner

*Primary Examiner* — Sujoy Kundu
*Assistant Examiner* — Harun Chowdhury
(74) *Attorney, Agent, or Firm* — Tyson B. Benson; Advent, LLP

(57) ABSTRACT

A computerized method for normalizing the results of clinical laboratory tests to a reference scale includes providing a measured value of a clinically significant parameter, providing a set of patient data, and providing a set of method data, including an indication of a method used by a testing instrument used to measure the measured value. One or more correlation factors are retrieved including a method correlation factor from a computer readable database based on the method data. The method correlation factor corresponds to the method used by the testing instrument used to measure the measured value. A normalized value of the clinically significant parameter is calculated based upon the one or more correlation factors. The normalized value may correspond to a value on the reference scale regardless of the method used by the testing instrument.

14 Claims, 11 Drawing Sheets

METHOD FOR NORMALIZING CLINICAL LABORATORY MEASUREMENTS

CROSS-REFERENCE TO RELATED APPLICATIONS

This application is a non-provisional application claiming priority to U.S. Application Ser. No. 61/255,979 filed on Oct. 29, 2009, titled METHOD FOR NORMALIZING CLINICAL LABORATORY MEASUREMENTS which is incorporated by reference herein in its entirety.

BACKGROUND OF THE INVENTION

The present invention relates generally to a method of normalizing clinical laboratory measurements. In particular, the present invention relates to a method of normalizing clinical laboratory measurements across a range of measurement devices and methods.

Medical practitioners including physicians utilize clinical laboratory measurements in making treatment decisions and diagnostic determinations for patients. These measurements are generally made using a variety of techniques that may directly measure the amount of a target compound in blood or urine, or they may indirectly measure the amount of a target compound by using a reagent to produce a secondary compound that can be measured more easily and/or accurately than the target compound. The target compounds may be electrolytes, enzymes, antibodies, or other compounds of clinical interest.

Currently, clinical laboratory measurements are compared to a reference range. The reference range provides a range of values for a particular measurement that is considered normal and is defined by a maximum value and a minimum value. The reference range for a particular measurement may vary from one clinical laboratory to another depending on the testing equipment used, the lot number of any reagents used, and the date on which the measurement is taken. Each time a new reagent lot number is used, a new reference range must be determined for the method and testing instrument being used by employing reference samples for calibration.

As a result, the measured value of a target compound provided by a particular testing method is not useful as an absolute measurement, but only as the measured value compares to a specific reference range that will vary depending on the lot number of reagent used. In addition, the reference range for "normal" valued may vary for patients of different demographic groups. For example, a physician may recommend medical intervention for a patient who is 60 years old with a particular measured cholesterol level and forgo medical intervention for a 20 year old patient with the same measured cholesterol level. This shows that the reference ranges for some measured values are only useful for particular age groups.

The fact that the measured values and reference ranges may vary from laboratory to laboratory and from patient to patient results in a complicated evaluation for physicians and other medical practitioners when it comes to evaluating medical decision points. Such complexity not only consumes resources, but makes the sharing of information between facilities difficult and increases the chance of medical errors.

Accordingly, there is a need for a method of normalizing clinical laboratory measurements that simplifies the process of comparing a level of a target compound to a reference range.

SUMMARY OF THE INVENTION

A computerized method for normalizing the results of clinical laboratory tests to a reference scale includes providing a measured value of a clinically significant parameter, providing a set of patient data, and providing a set of method data, including an indication of a method used by a testing instrument used to measure the measured value. One or more correlation factors are retrieved including a method correlation factor from a computer readable database based on the method data. The method correlation factor corresponds to the method used by the testing instrument used to measure the measured value. A normalized value of the clinically significant parameter is calculated based upon the one or more correlation factors. The normalized value may correspond to a value on the reference scale where the scale includes maximum and minimum allowable limits for the normalized value regardless of the method used by the testing instrument.

DETAILED DESCRIPTION OF THE INVENTION

Figure 2A:
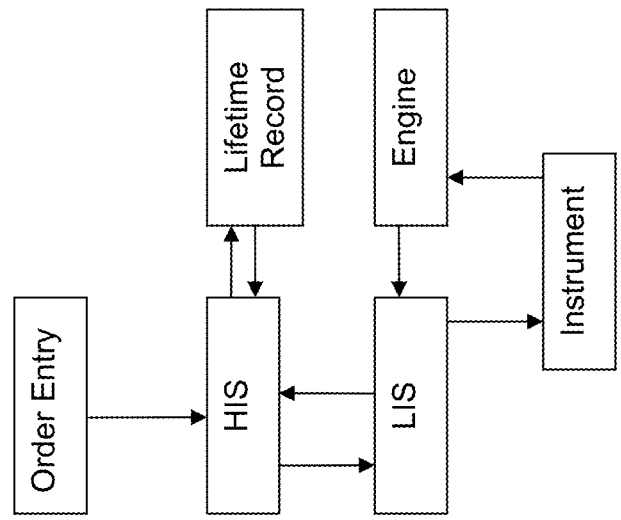
FIGS. 2a-2d are flow diagrams for the process of FIG. 1 including automatic normalization of a measured value.

The present method allows for changes to clinical laboratory methods and equipment while allowing a physician or other medical practitioner to use the same medical decision points when evaluating the results of clinical laboratory tests. In order to allow medical practitioners who use different laboratories with different equipment to evaluate a clinical laboratory measurements against a single reference range.

Variations in laboratory measurements are more extreme for certain types of tests than others. For example, measurements of electrolytes using different clinical methods will not be as disparate as measurements of enzyme or antibody levels done by different methods.

In particular, linear regression methods can be used to normalize measured values. In these methods, a single method of measuring a clinically important value may be selected as a "gold standard" (i.e. the standard method) against which other methods may be normalized. Once normalized, measured values may be compared to the reference range for the "gold standard" method for purposes of making medical decisions. In some methods, a measured value Xm may be normalized according to a linear equation to provide a normalized value XF according to the equation where $M_{mfg}$ is a correlation factor that equals the slope of the regression line used to correlate the measured value $X_m$ to a value provided by the standard method and $I_{mfg}$ is the vertical intercept of the line.

$$X_m*M_{mfg}+I_{mfg}=X_F$$

In most cases, the regression line will have an intercept of zero, in which case the intercept may be ignored.

While a particular method or equipment for measurement may be selected for the standard method, the normalized value may also be correlated for reagent lot number, patient age, date range during which the testing was completed, or other factors. In these methods, the normalized value $X_F$ may be determined by the following formula:

$$(X_m*M_{mfg}+I_{mfg})(A_m+I_A)(D_m+I_D)(L_M+I_L)=X_F$$

where $A_m$ is an age correlation factor (i.e. the slope of the regression line for correlating the age of a patient to a standard age and $I_A$ is the slope of that line; $D_m$ is a date range correlation factor (i.e. the slope of the regression line for correlating the date range during which the testing was done to a standard date and $I_D$ is the intercept of that line; and $L_M$ is a lot number correlation factor (i.e. the slope of the regression line for correlating the lot number of a reagent used in a particular method to a standard lot number and $I_L$ is the intercept of that line. Again, the intercepts of the various lines should approximate zero, so the formula simplifies to:

$$X_m*M_{mfg}*A_m*D_m*L_M=X_F$$

The correlation factors above would need to be determined by regression analysis done for each specific method being done. In other words, the age correlation for one method may be different than for another. Accordingly, a computer accessible library would be useful for storing and accessing the correlation factors for a variety of methods so that they may be used to calculate the normalized value. In some embodiments of the invention, chemical reagent manufacturers could provide reagent lot number correlation factors to a centralized system that could then make those correlation factors available to clinical laboratories on a subscription basis. Providing access to these correlation factors would lessen the need for, or compliment, internal validations done by clinical laboratories when they begin to use a new lot number of a reagent.

The correlation factors may be calculated by using one of a variety of linear regression models. A standard regression may be carried out, however, such a model does not account for random error that may be present in the data. Such errors, may be transcription errors, equipment errors, or errors attributable to a technician. Such errors can be accounted for by using a Deming regression model which is the preferred regression model for use with the methods described, especially when the data being normalized is produced by methods that are similar to the standard method.

In a preferred embodiment, a clinical test utilizing a particular method, employing a particular lot number of reagent, within a particular date range, and for a patient of a particular age would be used to measure a value. This measured value would automatically be normalized against a standard method based on test method, date range, lot number, and age correlation factors. The normalized value could then be used with the reference range for the standard method to make medical decisions. All of the information about the test method, reagent lot number, date range, and patient age could be maintained in an electronic health record and/or a laboratory information system so that the normalization process could be completely automated.

Figure 1:
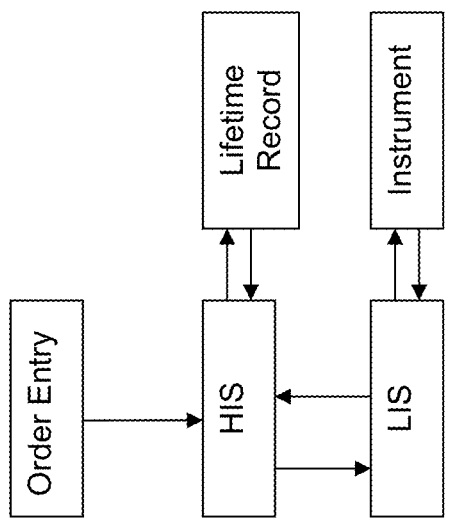
FIG. 1 is a flow diagram for the process of ordering and carrying out a clinical laboratory test within an electronic health record management system.

Referring to FIG. 1 a system for ordering and carrying out a clinical laboratory test within an electronic health record management system is provided. Orders for a laboratory test are entered into the system and transmitted to a Health Information System (HIS). The HIS relays the orders to a Laboratory Information System (LIS) which is coupled to an instrument. A laboratory technician utilizes the instrument to perform the ordered test on a specimen. The Instrument then relays the results of the test to the LIS which in turn sends the results to the HIS. The HIS may access a patient's Lifetime Record that is stored in a database and update the Lifetime Record with the test results. A notification may be sent to the person who entered the test orders that the test results are available for review.

Referring to FIG. 2, a system for ordering and carrying out a clinical laboratory test within an electronic health record management system includes the addition of a normalization Engine. The Engine may be incorporated into the system at one of several positions.

For example, in FIG. 2a, an order for a clinical laboratory test is entered into the HIS. The HIS relays the orders to a LIS which is coupled to an instrument. A laboratory technician utilizes the instrument to perform the ordered test on a specimen. The Instrument then relays the results of the test to the Engine which normalizes the results against a reference range. The normalized result is then passed to the LIS which in turn sends the normalized result to the HIS. The HIS may access a patient's Lifetime Record that is stored in a database and update the Lifetime Record with the normalized result. A notification may be sent to the person who entered the test orders that the test results are available for review.

Figure 2D:
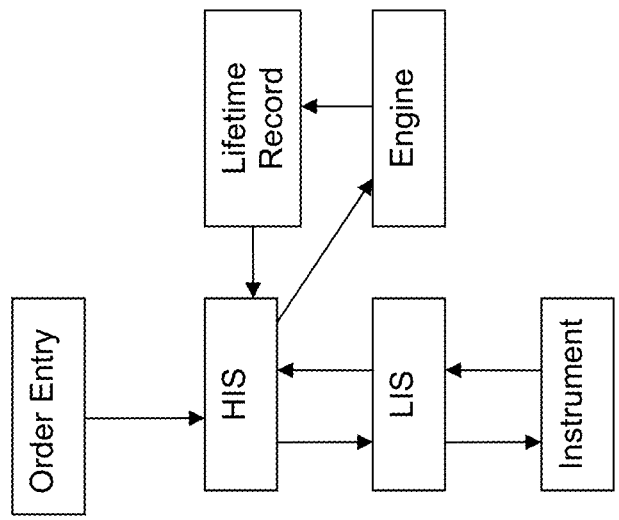
Figure 2C:
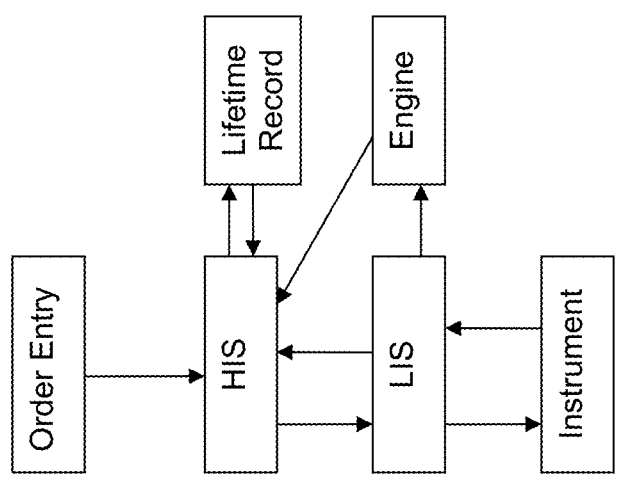
Figure 2B:
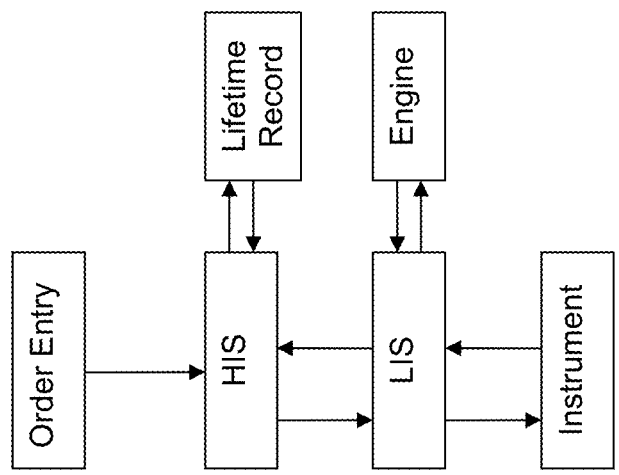

In FIG. 2b, the Engine may be configured to receive raw results from the LIS after they are reported from the instrument. The Engine normalized the results and returns the normalized results to the LIS. The LIS then provides the normalizes results to the HIS. As shown in FIG. 2c, the engine may be configured to receive raw results from the LIS after they are reported from the instrument. The Engine may then provide the normalized results directly to the HIS rather than to the LIS. Alternatively, as shown in FIG. 2d, the Engine may be configured to receive test results from the HIS, normalize those results against a reference range, and pass the normalized values to the database holding the patient's Lifetime Record.

Example 1

Figure 3:
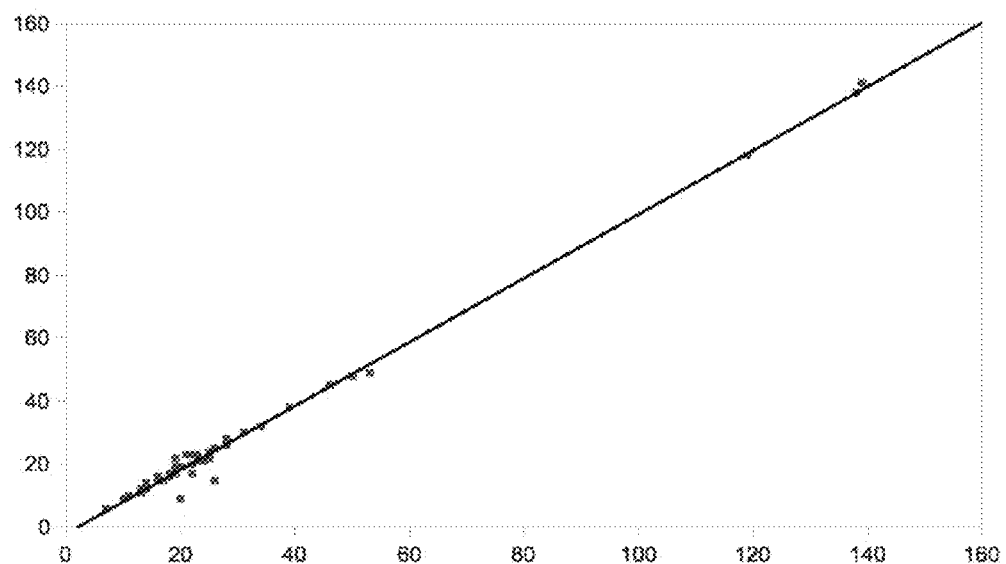
FIG. 3 is a chart showing a linear regression for correlating two separate methods for measuring blood urea nitrogen.

Referring to FIG. 3, a plot of a regression curve is shown for the data below in Table 1. A reference test methodology and instrument, i.e. a "gold standard", is used to provide a reference measurement for a specimen. A second test is also performed using a different instrument and methodology to provide a second measured value. Deming regression was used to provide a linear equation that can in turn be used to calculate a normalized value approximating that which would be obtained by using the "gold standard" from a value measured by the second methodology. In this case, the clinically significant parameter being measured was blood urea nitrogen. The "gold standard" instrument used for the 'Y' method was a Beckman Coulter DXC 880i using the manufacturer's standard methodology. The second test yielding the 'X' values was conducted on a Johnson & Johnson VITROS 5.1 instrument using the manufacturer's standard methodology. These two methodologies' instruments were used for all tests in the following examples and are consistently referred to as the 'X' or 'Y' methods or instruments. All reagents were from the same lot numbers by method and manufacturer, and the testing was all conducted on the same day.

TABLE 1

| Specimen | X | Y |
|---|---|---|
| 1 | 21 | 23 |
| 2 | 28 | 28 |
| 3 | 16 | 16 |
| 4 | 23 | 22 |
| 5 | 22 | 23 |
| 6 | 10 | 9 |
| 7 | 16 | 15 |
| 8 | 13 | 11 |
| 9 | 25 | 24 |
| 10 | 7 | 6 |
| 11 | 10 | 9 |
| 12 | 23 | 23 |
| 13 | 26 | 25 |
| 14 | 31 | 30 |
| 15 | 14 | 12 |
| 16 | 25 | 23 |
| 17 | 17 | 15 |
| 18 | 39 | 38 |
| 19 | 20 | 19 |
| 20 | 34 | 32 |
| 21 | 11 | 10 |
| 22 | 23 | 21 |
| 23 | 19 | 22 |
| 24 | 25 | 22 |
| 25 | 46 | 45 |
| 26 | 14 | 14 |
| 27 | 13 | 11 |
| 28 | 22 | 20 |
| 29 | 18 | 17 |
| 30 | 16 | 15 |
| 31 | 23 | 22 |
| 32 | 13 | 12 |
| 33 | 18 | 16 |
| 34 | 22 | 17 |
| 35 | 28 | 27 |
| 36 | 18 | 17 |
| 37 | 53 | 49 |
| 38 | 24 | 21 |
| 39 | 19 | 19 |
| 40 | 19 | 17 |
| 81 | 133 | 138 |
| 82 | 28 | 26 |
| 83 | 50 | 48 |
| 84 | 139 | 141 |
| 85 | 119 | 118 |

A Deming regression analysis of the data shown in Table 1 provides a slope of 0.1025 (with a 95% confidence interval of 1.009 to 1.041) and an intercept of −1.7 (with a 95% confidence interval of −2.4 to −1.1). In this case the a normalized value for a test done on the VITROS 5.1 would be calculated from the equation:

$$X_m * M_{mfg} + I_{mfg} = X_F$$

where $X_m$ is the value measured on the VITROS 5.1, $M_{mfg}$ is 1.025, $I_{mfg}$ is −1.7 and $X_F$ is the normalized value which corresponds to a value that would likely have been measured on the DXC 880i. This normalized value may then be used with reference ranges established for interpreting measurements made with the DXC 880i.

It should be noted that the bias or difference between the measured value and the corresponding value on the reference range is relatively small giving a slope for the regression curve close to 1 and an intercept close to the origin. Several different clinical tests will have small biases including electrolyte measurements.

Example 2

Figure 4:
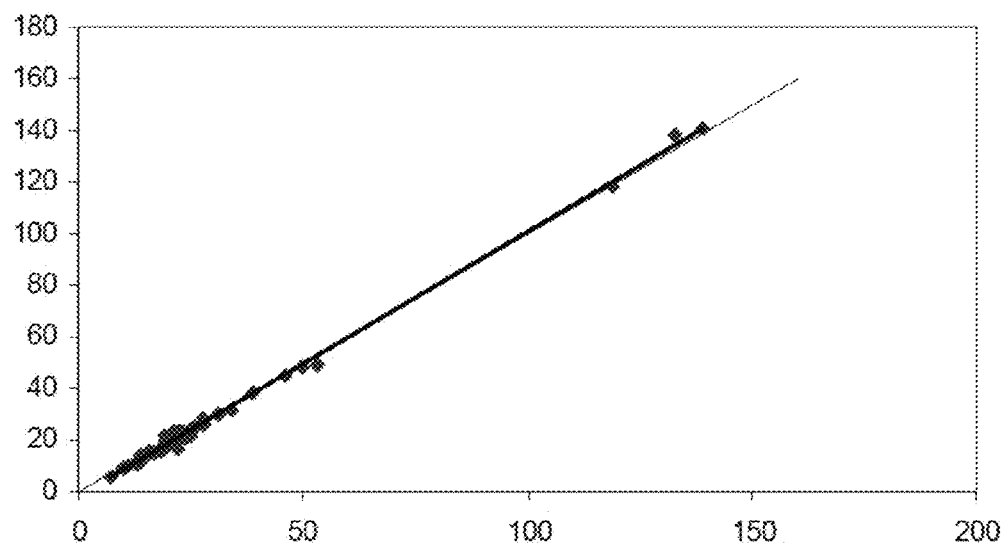
FIG. 4 is a chart showing a linear regression for correlating two separate methods for measuring albumin.

Referring to FIG. 4, a plot of regression curve is shown for the data below in Table 2. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was albumin.

TABLE 2

| Specimen | X | Y |
|---|---|---|
| 1 | 21 | 23 |
| 2 | 28 | 28 |
| 3 | 16 | 16 |
| 4 | 23 | 22 |
| 5 | 22 | 23 |
| 6 | 10 | 9 |
| 7 | 16 | 15 |
| 8 | 13 | 11 |
| 9 | 25 | 24 |
| 10 | 7 | 6 |
| 11 | 10 | 9 |
| 12 | 23 | 23 |
| 13 | 26 | 25 |
| 14 | 31 | 30 |
| 15 | 14 | 12 |
| 16 | 25 | 23 |
| 17 | 17 | 15 |
| 18 | 39 | 38 |
| 19 | 20 | 19 |
| 20 | 34 | 32 |
| 21 | 11 | 10 |
| 22 | 23 | 21 |
| 23 | 19 | 22 |
| 24 | 25 | 22 |
| 25 | 46 | 45 |
| 26 | 14 | 14 |
| 27 | 13 | 11 |
| 28 | 22 | 20 |
| 29 | 18 | 17 |
| 30 | 16 | 15 |
| 31 | 23 | 22 |
| 32 | 13 | 12 |
| 33 | 18 | 16 |
| 34 | 22 | 17 |
| 35 | 28 | 27 |
| 36 | 18 | 17 |
| 37 | 53 | 49 |
| 38 | 24 | 21 |
| 39 | 19 | 19 |
| 40 | 19 | 17 |
| 81 | 133 | 138 |
| 82 | 28 | 26 |
| 83 | 50 | 48 |
| 84 | 139 | 141 |
| 85 | 119 | 118 |

A Deming regression analysis of the data shown in Table 2 provides a slope of 0.841 (with a 95% confidence interval of 0.773 to 0.944) and an intercept of 0.36 (with a 95% confidence interval of 0.03 to 0.70).

Example 3

Figure 5:
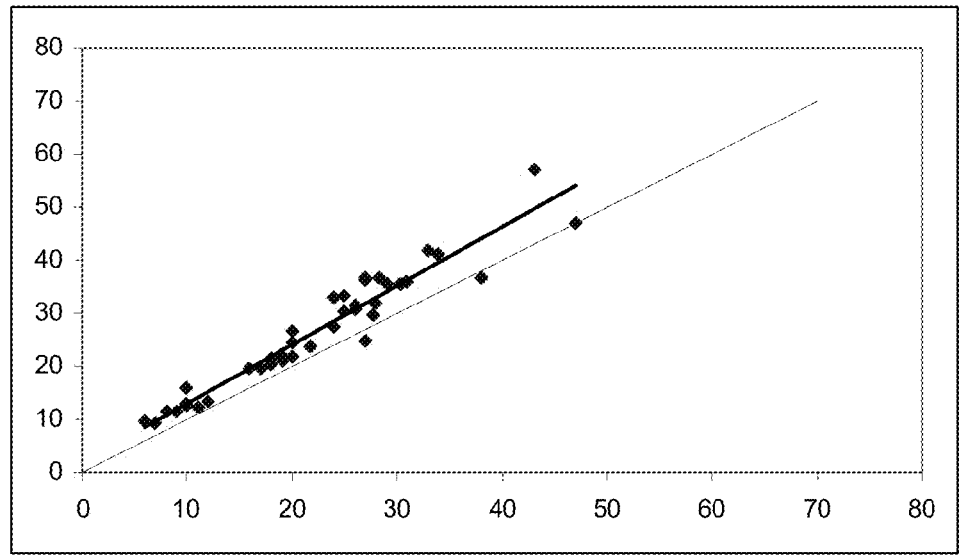
FIG. 5 is a chart showing a linear regression for correlating two separate methods for measuring high density lipoprotein.

Referring to FIG. 5, a plot of regression curve is shown for the data below in Table 2. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was high density lipoprotein.

TABLE 3

| Specimen | X | Y |
| --- | --- | --- |
| 1 | 25 | 25.9 |
| 2 | 27 | 30.7 |
| 3 | 19 | 21.9 |
| 4 | 31 | 32.9 |
| 5 | 43 | 50.1 |
| 6 | 41 | 41.3 |
| 7 | 18 | 19.9 |
| 8 | 52 | 55.5 |
| 9 | 42 | 4.8 |
| 10 | 43 | 45.8 |
| 11 | 33 | 35.1 |
| 12 | 23 | 26.1 |
| 13 | 31 | 30.2 |
| 14 | 26 | 29.9 |
| 15 | 22 | 24.8 |
| 16 | 32 | 35.1 |
| 17 | 30 | 33.6 |
| 18 | 40 | 48.4 |
| 19 | 42 | 47.6 |
| 20 | 37 | 37.8 |
| 21 | 44 | 46.5 |
| 22 | 41 | 44.7 |
| 23 | 13 | 15.2 |
| 24 | 43 | 46.8 |
| 25 | 30 | 30.3 |
| 26 | 24 | 27.1 |
| 27 | 46 | 47.4 |
| 28 | 43 | 44.6 |
| 29 | 35 | 35.7 |
| 30 | 54 | 53.8 |
| 31 | 41 | 40.5 |
| 32 | 47 | 53.1 |
| 33 | 61 | 53.4 |
| 34 | 37 | 41.3 |
| 35 | 50 | 51.9 |
| 36 | 22 | 28.9 |
| 37 | 26 | 26.4 |
| 38 | 49 | 52.2 |
| 39 | 17 | 24.1 |
| 40 | 49 | 16.7 |
| 62 | 27 | 23.3 |
| 63 | 23 | 22.9 |

A Deming regression analysis of the data shown in Table 3 provides a slope of 1.032 (with a 95% confidence interval of 0.960 to 1.104) and an intercept of 1.51 (with a 95% confidence interval of −1.1 to 4.1).

The standard error estimate is significantly greater than for either of the preceding examples, but the normalized values are still clinically useful for comparison to the reference range. Clinical tests, such as measuring antibodies, provide greater deviation than those for electrolytes as shown by the greater spread of the plotted data and correlation coefficient for the regression curve. These tests may be the ones where regression analysis is more prone to error, but comparison to a reference range is exceptionally useful due to the variance that results from differing instruments and methodologies.

Example 4

Figure 6:
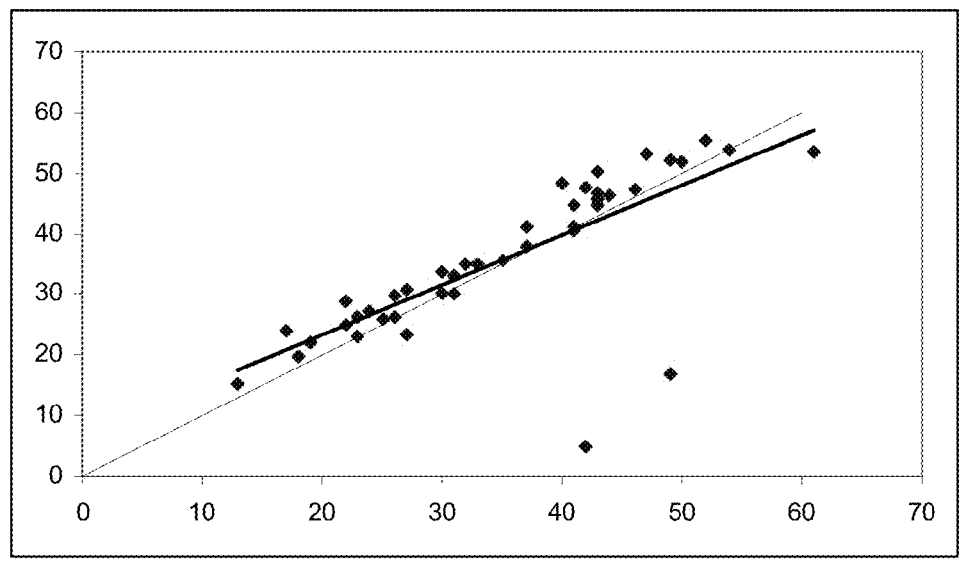
FIG. 6 is a chart showing a linear regression for correlating two separate methods for measuring complement 4.

Referring to FIG. 6, a plot of regression curve is shown for the data below in Table 4. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was C4 (complement 4).

TABLE 4

| Specimen | X | Y |
| --- | --- | --- |
| 1 | 26 | 31.4 |
| 2 | 26.9 | 36.7 |
| 3 | 17 | 19.8 |
| 4 | 8 | 11.3 |
| 5 | 25 | 33.4 |
| 6 | 18 | 21.5 |
| 7 | 28 | 31.7 |
| 8 | 6 | 9.6 |
| 9 | 33 | 42 |
| 10 | 26 | 30.6 |
| 11 | 24 | 32.9 |
| 12 | 30.3 | 35.7 |
| 13 | 38 | 36.5 |
| 14 | 27 | 24.8 |
| 15 | 19.2 | 21.2 |
| 16 | 27.7 | 29.6 |
| 17 | 21.8 | 23.6 |
| 18 | 34 | 41 |
| 19 | 16 | 19.5 |
| 20 | 19 | 22.1 |
| 21 | 27 | 36.2 |
| 22 | 20 | 24.5 |
| 23 | 25 | 30.5 |
| 24 | 29 | 35.7 |
| 25 | 20 | 26.6 |
| 26 | 9 | 11.5 |
| 27 | 28.2 | 36.5 |
| 28 | 47 | 47 |
| 29 | 43 | 57.2 |
| 30 | 31 | 35.8 |
| 31 | 10 | 15.8 |
| 32 | 18 | 20.2 |
| 33 | 10 | 12.7 |
| 34 | 29 | 35.7 |
| 35 | 11 | 12.1 |
| 36 | 20 | 22 |
| 37 | 24 | 27.3 |
| 38 | 10 | 13 |
| 39 | 12 | 13.3 |
| 40 | 7 | 9.2 |

A Deming regression analysis of the data shown in Table 4 provides a slope of 1.158 (with a 95% confidence interval of 1.050 to 1.291) and an intercept of 0.88 (with a 95% confidence interval of −1.78 to 3.53).

Example 5

Figure 7:
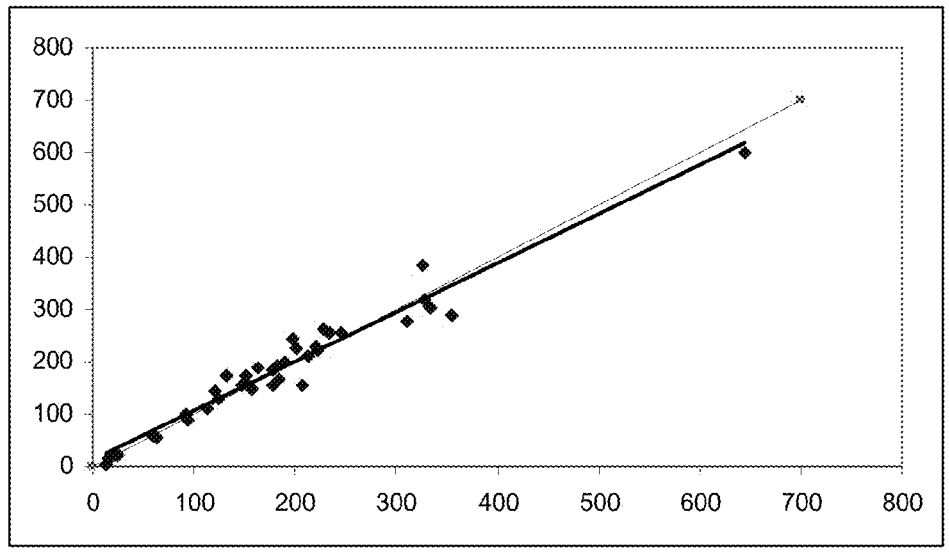
FIG. 7 is a chart showing a linear regression for correlating two separate methods for measuring haptoglobin.

Referring to FIG. 7, a plot of regression curve is shown for the data below in Table 5. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was haptoglobin.

TABLE 5

| Specimen | X | Y |
|---|---|---|
| 1 | 645 | 600 |
| 2 | 197 | 243 |
| 3 | 151 | 175 |
| 4 | 229 | 264 |
| 5 | 246 | 257 |
| 5 | 213 | 211 |
| 7 | 328 | 318 |
| 8 | 354 | 289 |
| 9 | 235 | 255 |
| 10 | 21 | 23 |
| 11 | 124 | 128 |
| 12 | 94 | 88 |
| 13 | 184 | 168 |
| 14 | 183 | 193 |
| 15 | 310 | 276 |
| 16 | 207 | 154 |
| 17 | 222 | 224 |
| 18 | 113 | 111 |
| 19 | 14 | 3 |
| 20 | 164 | 188 |
| 21 | 60 | 58 |
| 22 | 24 | 24 |
| 23 | 178 | 157 |
| 24 | 327 | 384 |
| 25 | 333 | 304 |
| 28 | 152 | 159 |
| 28 | 221 | 228 |
| 29 | 179 | 186 |
| 30 | 157 | 147 |
| 31 | 63 | 56 |
| 32 | 93 | 99 |
| 33 | 201 | 225 |
| 34 | 189 | 199 |
| 36 | 16 | 16 |
| 37 | 133 | 174 |
| 38 | 120 | 144 |
| 39 | 147 | 156 |

A Deming regression analysis of the data shown in Table 5 provides a slope of 0.959 (with a 95% confidence interval of 0.889 to 1.029) and an intercept of 8.5 (with a 95% confidence interval of −6.8 to 23.8).

Example 6

Figure 8:
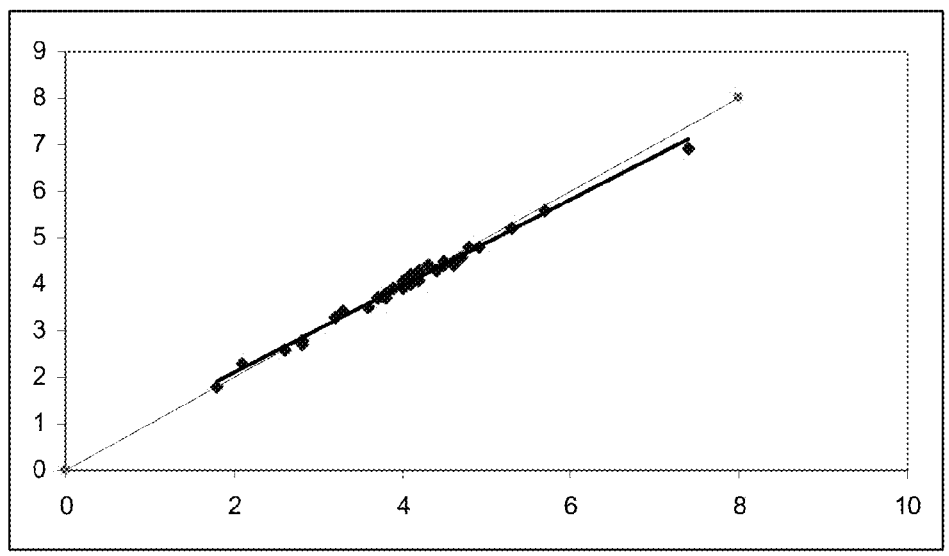
FIG. 8 is a chart showing a linear regression for correlating two separate methods for measuring potassium.

Referring to FIG. 8, a plot of regression curve is shown for the data below in Table 6. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was potassium.

TABLE 6

| Specimen | X | Y |
|---|---|---|
| 1 | 4.6 | 4.4 |
| 2 | 3.7 | 3.7 |
| 3 | 2.8 | 2.7 |
| 4 | 3.7 | 3.7 |
| 5 | 2.8 | 2.8 |
| 6 | 4.2 | 4.2 |
| 7 | 2.8 | 2.7 |
| 8 | 5.7 | 5.6 |
| 9 | 4 | 3.9 |
| 10 | 4.2 | 4.1 |
| 11 | 4 | 3.9 |
| 12 | 2.8 | 2.8 |
| 13 | 4 | 4.0 |
| 14 | 3.7 | 3.7 |
| 15 | 4.1 | 4.1 |
| 16 | 4 | 4.0 |
| 17 | 4.2 | 4.3 |
| 18 | 4.2 | 4.2 |
| 19 | 4.8 | 4.8 |
| 20 | 3.8 | 3.8 |
| 21 | 4.3 | 4.4 |
| 22 | 4.2 | 4.2 |
| 23 | 2.1 | 2.3 |
| 24 | 4.4 | 4.3 |
| 25 | 3.6 | 3.5 |
| 26 | 4.5 | 4.4 |
| 27 | 4.2 | 4.1 |
| 28 | 4.7 | 4.6 |
| 29 | 4.5 | 4.4 |
| 30 | 5.3 | 5.2 |
| 31 | 4.6 | 4.5 |
| 32 | 4.9 | 4.8 |
| 33 | 4.5 | 4.5 |
| 34 | 4.3 | 4.4 |
| 35 | 4.1 | 4.0 |
| 36 | 3.9 | 3.9 |
| 37 | 4.1 | 4.1 |
| 38 | 4.1 | 4.1 |
| 39 | 3.8 | 3.7 |
| 40 | 3.9 | 3.9 |
| 51 | 7.4 | 6.9 |
| 52 | 3.3 | 3.4 |
| 53 | 3.2 | 3.3 |
| 54 | 4.1 | 4.2 |
| 55 | 1.8 | 1.8 |
| 57 | 2.6 | 2.6 |
| 58 | 4 | 4.1 |

A Deming regression analysis of the data shown in Table 6 provides a slope of 0.935 (with a 95% confidence interval of 0.906 to 0.963) and an intercept of 0.23 (with a 95% confidence interval of 0.11 to 0.35).

Example 7

Figure 9:
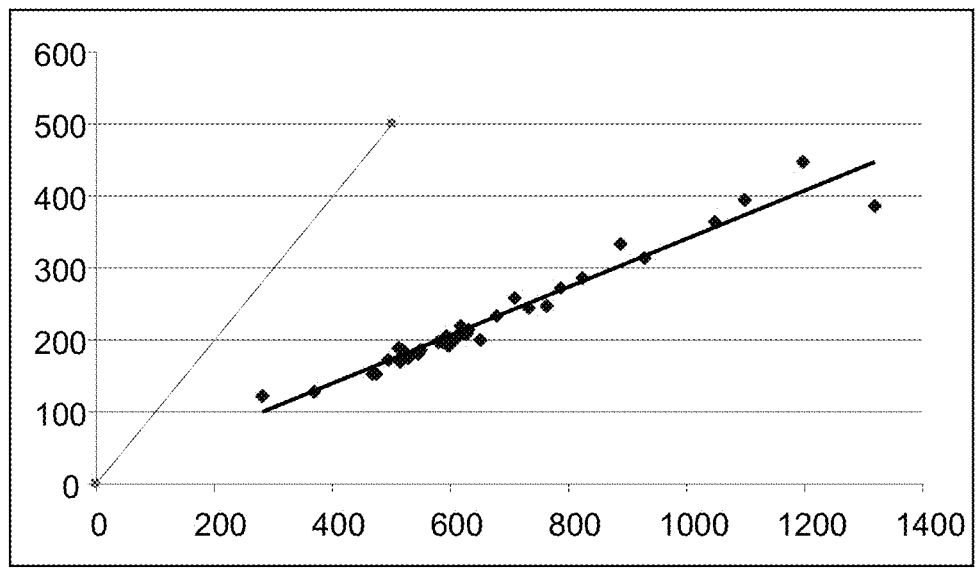
FIG. 9 is a chart showing a linear regression for correlating two separate methods for measuring low density lipoprotein.

Referring to FIG. 9, a plot of regression curve is shown for the data below in Table 7. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was low density lipoprotein.

TABLE 7

| Specimen | X | Y |
|---|---|---|
| 1 | 929 | 315 |
| 3 | 1318 | 387 |
| 4 | 605 | 197 |

TABLE 7-continued

| Specimen | X | Y |
| --- | --- | --- |
| 5 | 476 | 154 |
| 6 | 595 | 192 |
| 7 | 368 | 129 |
| 8 | 1196 | 447 |
| 9 | 545 | 180 |
| 10 | 762 | 248 |
| 11 | 468 | 152 |
| 12 | 516 | 175 |
| 13 | 626 | 210 |
| 14 | 620 | 212 |
| 15 | 549 | 187 |
| 16 | 1046 | 365 |
| 17 | 521 | 182 |
| 18 | 495 | 172 |
| 19 | 579 | 198 |
| 20 | 588 | 197 |
| 21 | 514 | 170 |
| 22 | 630 | 214 |
| 23 | 283 | 122 |
| 24 | 710 | 258 |
| 25 | 824 | 286 |
| 26 | 616 | 211 |
| 27 | 529 | 174 |
| 28 | 787 | 272 |
| 29 | 626 | 208 |
| 30 | 887 | 332 |
| 31 | 613 | 206 |
| 32 | 512 | 189 |
| 33 | 731 | 244 |
| 34 | 651 | 200 |
| 35 | 677 | 233 |
| 36 | 593 | 205 |
| 37 | 1098 | 394 |
| 38 | 547 | 181 |
| 39 | 618 | 219 |
| 40 | 520 | 186 |

A Deming regression analysis of the data shown in Table 7 provides a slope of 0.339 (with a 95% confidence interval of 0.315 to 0.363) and an intercept of 1.3 (with a 95% confidence interval of −15.3 to 17.9).

Example 8

Figure 10:
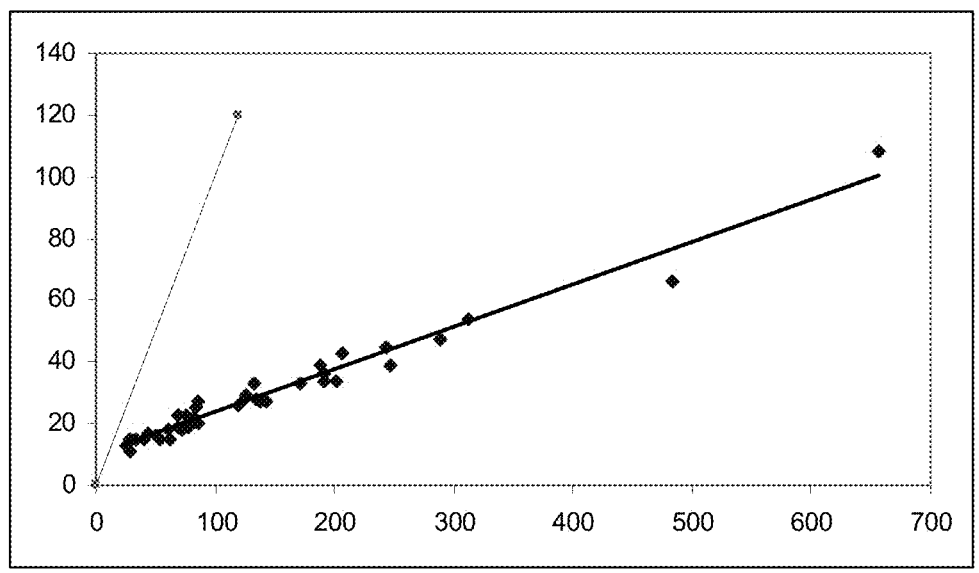
FIG. 10 is a chart showing a linear regression for correlating two separate methods for measuring blood lipid level.

Referring to FIG. 10, a plot of regression curve is shown for the data below in Table 8. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was a blood lipid level.

TABLE 8

| Specimen | X | Y |
| --- | --- | --- |
| 1 | 29 | 11 |
| 2 | 62 | 15 |
| 3 | 73 | 18 |
| 4 | 75 | 23 |
| 5 | 44 | 17 |
| 7 | 78 | 19 |
| 8 | 73 | 18 |
| 8 | 86 | 20 |
| 9 | 247 | 39 |
| 10 | 68 | 23 |
| 11 | 54 | 15 |
| 12 | 50 | 16 |
| 13 | 120 | 26 |
| 14 | 483 | 66 |
| 15 | 34 | 15 |
| 17 | 83 | 22 |
| 18 | 172 | 33 |
| 18 | 206 | 43 |
| 19 | 69 | 19 |
| 20 | 138 | 27 |
| 21 | 84 | 25 |
| 22 | 122 | 27 |
| 23 | 60 | 18 |
| 24 | 188 | 39 |
| 25 | 191 | 34 |
| 26 | 656 | 108 |
| 27 | 313 | 54 |
| 28 | 289 | 47 |
| 29 | 143 | 27 |
| 30 | 77 | 20 |
| 31 | 135 | 28 |
| 32 | 28 | 15 |
| 33 | 86 | 27 |
| 34 | 132 | 33 |
| 35 | 244 | 45 |
| 36 | 40 | 15 |
| 37 | 26 | 13 |
| 38 | 202 | 34 |
| 39 | 126 | 29 |
| 40 | 191 | 36 |

A Deming regression analysis of the data shown in Table 8 provides a slope of 0.136 (with a 95% confidence interval of 0.128 to 0.144) and an intercept of 10.1 (with a 95% confidence interval of 8.6 to 11.6).

Example 9

Figure 11:
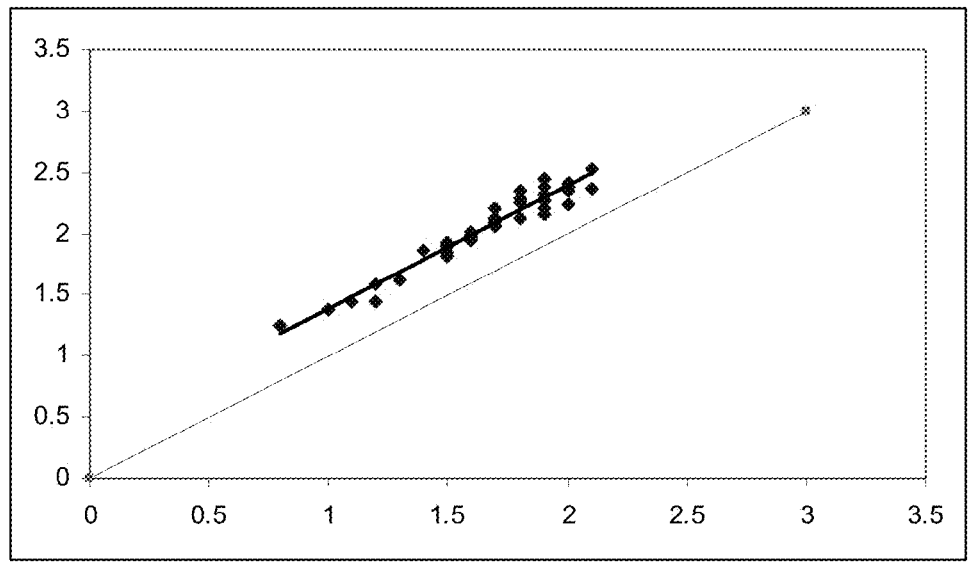
FIG. 11 is a chart showing a linear regression for correlating two separate methods for measuring magnesium.

Referring to FIG. 11, a plot of regression curve is shown for the data below in Table 9. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was magnesium.

TABLE 9

| Specimen | X | Y |
| --- | --- | --- |
| 1 | 1.3 | 1.62 |
| 2 | 1.7 | 2.05 |
| 3 | 1.1 | 1.44 |
| 4 | 1.9 | 2.27 |
| 5 | 1.2 | 1.45 |
| 6 | 1.5 | 1.90 |
| 7 | 1 | 1.38 |
| 8 | 1.8 | 2.29 |
| 9 | 1.6 | 2.01 |
| 10 | 1.7 | 2.09 |
| 11 | 1.8 | 2.13 |
| 12 | 1 | 1.37 |
| 13 | 1.5 | 1.82 |
| 14 | 1.5 | 1.84 |
| 15 | 1.2 | 1.59 |
| 16 | 1.9 | 2.27 |
| 17 | 1.5 | 1.91 |
| 18 | 2.0 | 2.35 |
| 19 | 1.4 | 1.87 |
| 20 | 1.9 | 2.21 |

TABLE 9-continued

| Specimen | X | Y |
| --- | --- | --- |
| 21 | 1.6 | 1.98 |
| 22 | 1.6 | 1.94 |
| 23 | 0.8 | 1.25 |
| 24 | 1.7 | 2.12 |
| 25 | 1.7 | 2.05 |
| 26 | 2.1 | 2.37 |
| 27 | 1.7 | 2.10 |
| 28 | 2.0 | 2.23 |
| 29 | 2.0 | 2.41 |
| 30 | 1.8 | 2.25 |
| 31 | 1.6 | 1.99 |
| 32 | 1.9 | 2.38 |
| 33 | 1.9 | 2.44 |
| 34 | 2.0 | 2.39 |
| 35 | 1.9 | 2.31 |
| 36 | 1.9 | 2.15 |
| 37 | 1.7 | 2.21 |
| 38 | 2.1 | 2.53 |
| 39 | 1.5 | 1.93 |
| 40 | 1.8 | 2.35 |

A Deming regression analysis of the data shown in Table 9 provides a slope of 0.1031 (with a 95% confidence interval of 0.955 to 1.107) and an intercept of 0.335 (with a 95% confidence interval of 0.208 to 0.463).

Example 10

Figure 12:
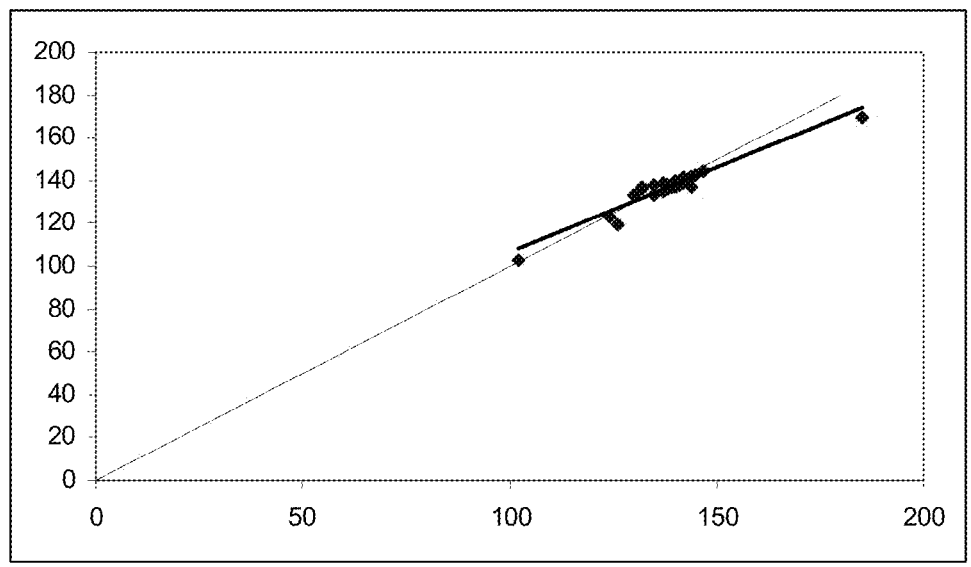
FIG. 12 is a chart showing a linear regression for correlating two separate methods for measuring sodium.

Referring to FIG. 12, a plot of regression curve is shown for the data below in Table 10. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was sodium.

TABLE 10

| Specimen | X | Y |
| --- | --- | --- |
| 2 | 124 | 123 |
| 4 | 144 | 142 |
| 5 | 142 | 142 |
| 6 | 144 | 142 |
| 7 | 102 | 103 |
| 8 | 141 | 138 |
| 9 | 142 | 139 |
| 10 | 139 | 137 |
| 11 | 140 | 137 |
| 13 | 138 | 136 |
| 14 | 138 | 136 |
| 15 | 142 | 141 |
| 16 | 140 | 139 |
| 17 | 140 | 140 |
| 18 | 140 | 138 |
| 19 | 140 | 139 |
| 20 | 140 | 139 |
| 21 | 141 | 140 |
| 22 | 138 | 137 |
| 24 | 141 | 139 |
| 25 | 139 | 137 |
| 26 | 147 | 144 |
| 27 | 143 | 140 |
| 28 | 140 | 139 |
| 29 | 138 | 137 |
| 30 | 143 | 139 |
| 31 | 143 | 140 |
| 32 | 145 | 143 |
| 33 | 144 | 142 |
| 34 | 142 | 141 |
| 35 | 137 | 135 |
| 36 | 137 | 135 |
| 37 | 138 | 138 |
| 38 | 138 | 137 |
| 39 | 135 | 133 |
| 40 | 144 | 137 |
| 51 | 126 | 119 |
| 52 | 132 | 137 |
| 53 | 137 | 139 |
| 54 | 185 | 169 |
| 55 | 135 | 138 |
| 55 | 132 | 136 |
| 57 | 130 | 133 |

A Deming regression analysis of the data shown in Table 10 provides a slope of 0.1009 (with a 95% confidence interval of 0.917 to 1.101) and an intercept of −2.4 (with a 95% confidence interval of −15.2 to 10.4).

Example 11

Figure 13:
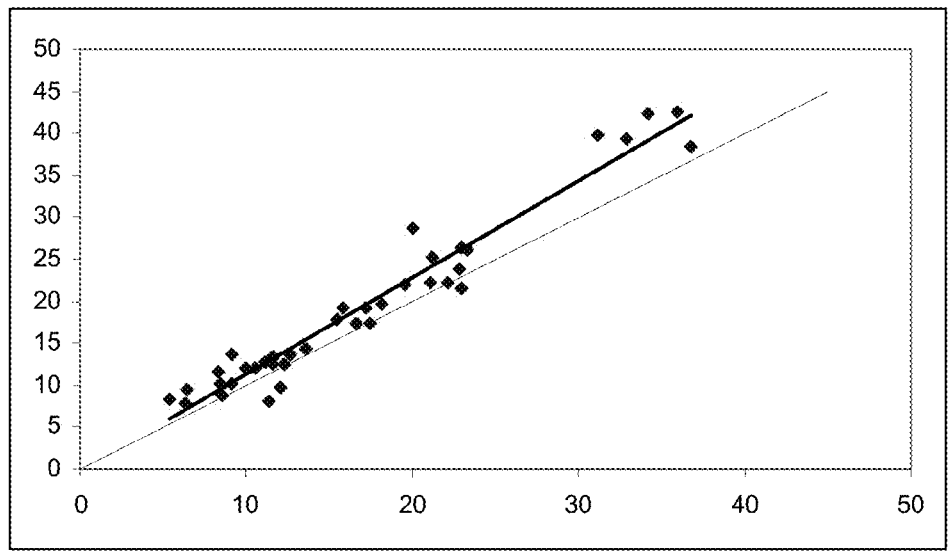
FIG. 13 is a chart showing a linear regression for correlating two separate methods for measuring pre-albumin.

Referring to FIG. 13, a plot of regression curve is shown for the data below in Table 11. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was pre-albumin.

TABLE 11

| Specimen | X | Y |
| --- | --- | --- |
| 1 | 11.6 | 12.6 |
| 2 | 8.6 | 8.8 |
| 3 | 11.3 | 8 |
| 4 | 11.6 | 13.4 |
| 5 | 22.9 | 21.5 |
| 6 | 6.4 | 9.4 |
| 7 | 12.1 | 9.8 |
| 8 | 9.1 | 10.3 |
| 9 | 5.4 | 8.3 |
| 10 | 36.8 | 38.4 |
| 11 | 15.8 | 19.3 |
| 12 | 22.1 | 22.2 |
| 13 | 15.5 | 17.8 |
| 14 | 32.9 | 39.4 |
| 15 | 10.5 | 12 |
| 16 | 17.2 | 19.2 |
| 17 | 18.2 | 19.7 |
| 18 | 16.6 | 17.3 |
| 19 | 20 | 28.8 |
| 20 | 22.9 | 26.4 |
| 21 | 11.1 | 12.8 |
| 22 | 12.6 | 13.7 |
| 23 | 19.6 | 22.1 |
| 24 | 17.4 | 17.3 |
| 25 | 22.8 | 23.8 |
| 26 | 35.9 | 42.5 |
| 27 | 21.2 | 25.2 |
| 28 | 13.6 | 14.3 |
| 28 | 12.3 | 12.5 |
| 30 | 8.3 | 11.5 |
| 31 | 9.1 | 13.7 |
| 32 | 6.3 | 7.8 |
| 33 | 23.3 | 26.2 |

TABLE 11-continued

| Specimen | X | Y |
|---|---|---|
| 34 | 9.9 | 12 |
| 35 | 21.1 | 22.3 |
| 36 | 31.1 | 39.7 |
| 37 | 34.2 | 42.4 |
| 38 | 11.6 | 13.3 |
| 39 | 8.4 | 10.2 |
| 40 | 11.5 | 13.1 |

A Deming regression analysis of the data shown in Table 11 provides a slope of 1.185 (with a 95% confidence interval of 1.100 to 1.270) and an intercept of −0.95 (with a 95% confidence interval of −2.54 to 0.63).

Example 12

Figure 14:
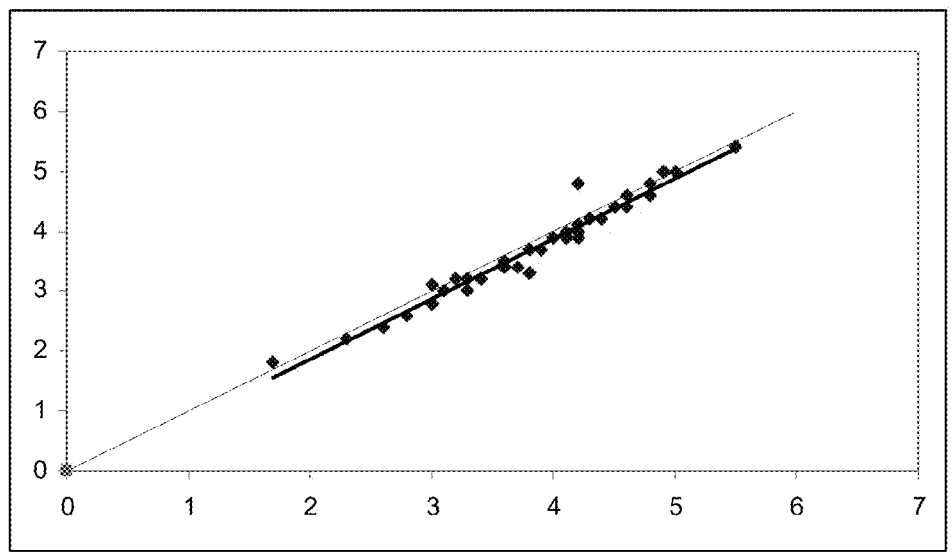
FIG. 14 is a chart showing a linear regression for correlating two separate methods for measuring phosphorus.

Referring to FIG. 14, a plot of regression curve is shown for the data below in Table 12. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was phosphorus.

TABLE 12

| Specimen | X | Y |
|---|---|---|
| 1 | 4.1 | 3.9 |
| 2 | 5.0 | 5.0 |
| 3 | 3.0 | 2.8 |
| 4 | 3.7 | 3.4 |
| 5 | 2.3 | 2.2 |
| 7 | 2.6 | 2.4 |
| 8 | 4 | 3.9 |
| 8 | 4.2 | 3.9 |
| 9 | 4.4 | 4.2 |
| 10 | 3.4 | 3.2 |
| 11 | 3.9 | 3.7 |
| 12 | 3 | 2.8 |
| 13 | 3.2 | 3.2 |
| 14 | 2.8 | 2.6 |
| 15 | 3.8 | 3.3 |
| 16 | 4.6 | 4.4 |
| 17 | 4.2 | 4.0 |
| 18 | 4.9 | 5.0 |
| 19 | 4.8 | 4.6 |
| 20 | 4.8 | 4.6 |
| 21 | 3.4 | 3.2 |
| 22 | 3.6 | 3.5 |
| 23 | 1.7 | 1.8 |
| 24 | 3.3 | 3.2 |
| 25 | 4.5 | 4.4 |
| 26 | 3.3 | 3.0 |
| 27 | 3.6 | 3.4 |
| 28 | 5.5 | 5.4 |
| 29 | 4.3 | 4.2 |
| 30 | 3.6 | 3.4 |
| 31 | 4.1 | 4.0 |
| 32 | 3.8 | 3.7 |
| 33 | 4.6 | 4.6 |
| 34 | 3.9 | 3.7 |
| 36 | 4.8 | 4.8 |
| 36 | 3.1 | 3.0 |
| 37 | 4.2 | 4.0 |
| 38 | 4.2 | 4.1 |
| 39 | 3.0 | 3.1 |
| 40 | 4.2 | 4.8 |

A Deming regression analysis of the data shown in Table 12 provides a slope of 1.039 (with a 95% confidence interval of 0.973 to 1.104) and an intercept of −0.26 (with a 95% confidence interval of −0.52 to −0.01).

Example 13

Figure 15:
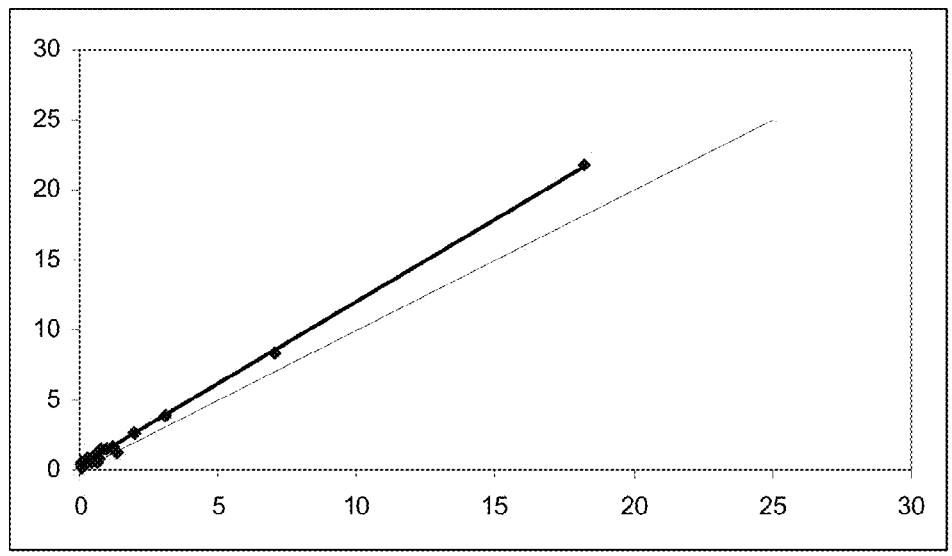
FIG. 15 is a chart showing a linear regression for correlating two separate methods for measuring bilirubin.

Referring to FIG. 15, a plot of regression curve is shown for the data below in Table 13. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was total bilirubin.

TABLE 13

| Specimen | X | Y |
|---|---|---|
| 1 | 0.1 | 0.5 |
| 2 | 0.2 | 0.7 |
| 3 | 0.1 | 0.6 |
| 4 | 0.2 | 0.6 |
| 5 | 0.5 | 1.0 |
| 6 | 0.1 | 0.6 |
| 7 | 0.1 | 0.4 |
| 8 | 1.3 | 1.2 |
| 9 | 0.3 | 0.6 |
| 10 | 0.5 | 0.7 |
| 11 | 0.1 | 0.2 |
| 12 | 0.1 | 0.3 |
| 13 | 3.1 | 3.9 |
| 14 | 0.7 | 0.9 |
| 15 | 0.2 | 0.6 |
| 17 | 0.6 | 0.9 |
| 18 | 0.4 | 0.5 |
| 18 | 2 | 2.6 |
| 19 | 1.2 | 1.7 |
| 20 | 0.5 | 0.8 |
| 21 | 1 | 1.5 |
| 22 | 0.3 | 0.8 |
| 23 | 0.7 | 1.3 |
| 24 | 0.6 | 0.8 |
| 25 | 0.4 | 0.8 |
| 26 | 0.2 | 0.7 |
| 27 | 0.3 | 0.7 |
| 28 | 0.3 | 0.5 |
| 30 | 0.8 | 1.5 |
| 31 | 0.1 | 0.4 |
| 32 | 0.6 | 0.9 |
| 33 | 0.6 | 0.8 |
| 34 | 0.6 | 0.6 |
| 35 | 0.2 | 0.4 |
| 36 | 0.3 | 0.5 |
| 37 | 1.2 | 1.7 |
| 38 | 1.2 | 1.5 |
| 39 | 7.0 | 8.3 |
| 40 | 18.2 | 21.8 |

A Deming regression analysis of the data shown in Table 13 provides a slope of 1.180 (with a 95% confidence interval of 1.160 to 1.180) and an intercept of 0.24 (with a 95% confidence interval of 0.18 to 0.31).

Example 14

Figure 16:
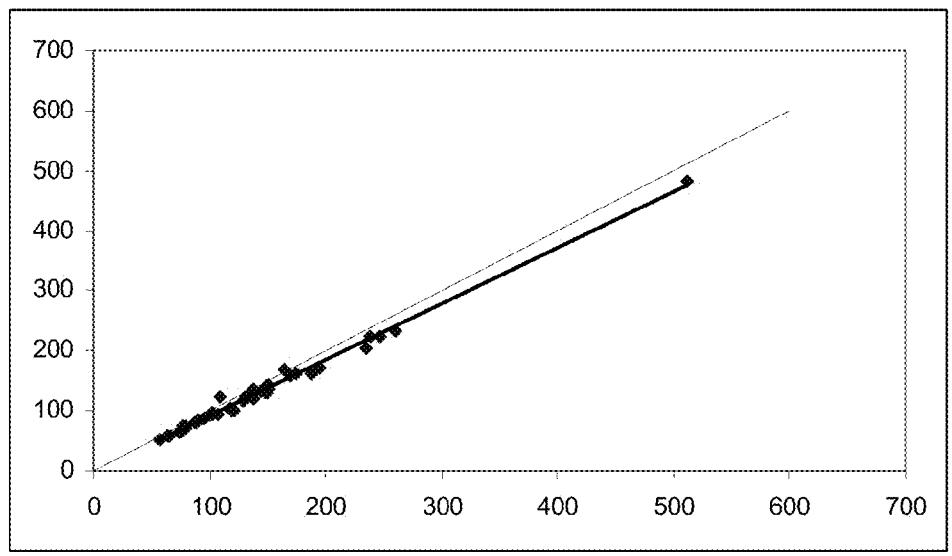
FIG. 16 is a chart showing a linear regression for correlating two separate methods for measuring triglyceride level.

Referring to FIG. 16, a plot of regression curve is shown for the data below in Table 14. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was a triglyceride level.

TABLE 14

| Specimen | X | Y |
|---|---|---|
| 1 | 91 | 85 |
| 2 | 136 | 128 |
| 3 | 138 | 136 |
| 4 | 246 | 225 |
| 5 | 65 | 57 |
| 6 | 238 | 225 |
| 7 | 131 | 122 |
| 8 | 121 | 100 |
| 9 | 108 | 94 |
| 10 | 74 | 64 |
| 11 | 512 | 482 |
| 12 | 57 | 51 |
| 13 | 89 | 82 |
| 14 | 63 | 57 |
| 15 | 96 | 86 |
| 16 | 77 | 73 |
| 17 | 130 | 118 |
| 18 | 103 | 94 |
| 19 | 151 | 136 |
| 20 | 144 | 134 |
| 21 | 75 | 66 |
| 22 | 87 | 80 |
| 23 | 109 | 124 |
| 24 | 118 | 103 |
| 25 | 119 | 102 |
| 26 | 194 | 171 |
| 27 | 137 | 120 |
| 28 | 188 | 162 |
| 29 | 149 | 131 |
| 30 | 235 | 204 |
| 31 | 260 | 234 |
| 32 | 79 | 73 |
| 33 | 138 | 129 |
| 34 | 151 | 143 |
| 35 | 170 | 159 |
| 36 | 149 | 144 |
| 37 | 103 | 98 |
| 38 | 79 | 72 |
| 39 | 100 | 95 |
| 40 | 175 | 163 |
| 81 | 164 | 168 |

A Deming regression analysis of the data shown in Table 14 provides a slope of 0.936 (with a 95% confidence interval of 0.907 to 0.964) and an intercept of −2.1 (with a 95% confidence interval of −6.7 to 2.5).

Example 15

Figure 17:
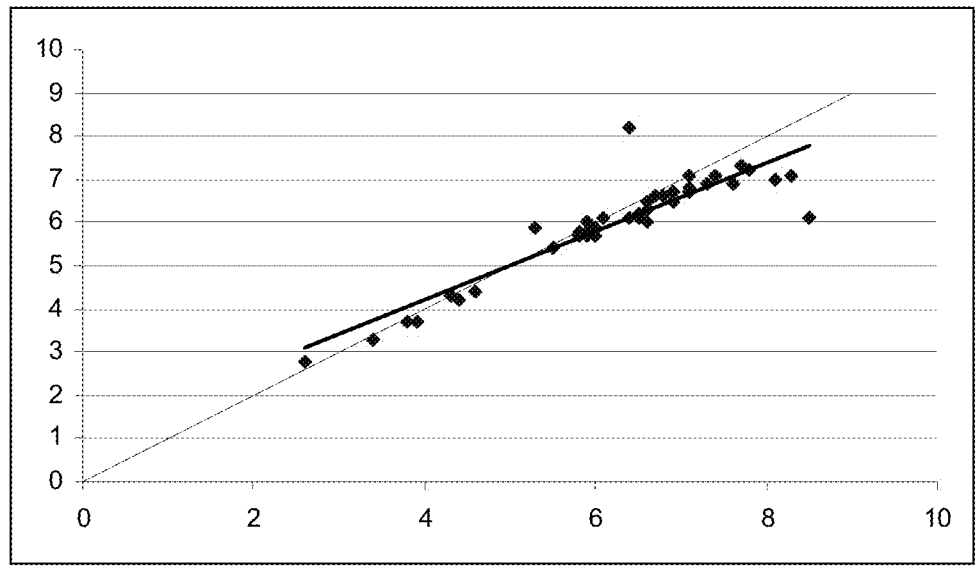
FIG. 17 is a chart showing a linear regression for correlating two separate methods for measuring total protein.

Referring to FIG. 17, a plot of regression curve is shown for the data below in Table 15. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was total protein.

TABLE 15

| Specimen | X | Y |
|---|---|---|
| 1 | 3.8 | 3.7 |
| 2 | 4.6 | 4.4 |
| 3 | 3.9 | 3.7 |
| 4 | 6.5 | 6.2 |
| 5 | 4.4 | 4.2 |
| 6 | 6.6 | 6.0 |
| 7 | 4.3 | 4.3 |
| 8 | 8.3 | 7.1 |
| 9 | 6.8 | 6.6 |
| 10 | 6.9 | 6.5 |
| 11 | 6.6 | 6.3 |
| 12 | 3.4 | 3.3 |
| 13 | 6.1 | 6.1 |
| 14 | 5.8 | 5.7 |
| 15 | 5.8 | 5.8 |
| 16 | 5.5 | 5.4 |
| 17 | 5.3 | 5.9 |
| 18 | 6.4 | 8.2 |
| 19 | 8.5 | 6.1 |
| 20 | 5.9 | 5.8 |
| 21 | 6.7 | 6.6 |
| 22 | 5.9 | 5.7 |
| 23 | 2.6 | 2.8 |
| 24 | 7.1 | 6.8 |
| 25 | 6.0 | 5.7 |
| 26 | 6.5 | 6.2 |
| 27 | 7.1 | 6.7 |
| 28 | 6.6 | 6.5 |
| 29 | 6.4 | 6.1 |
| 30 | 8.1 | 7.0 |
| 31 | 7.3 | 6.9 |
| 32 | 7.7 | 7.3 |
| 33 | 7.8 | 7.2 |
| 34 | 7.1 | 7.1 |
| 35 | 6.9 | 6.7 |
| 36 | 5.9 | 6.0 |
| 37 | 6.5 | 6.1 |
| 38 | 7.4 | 7.1 |
| 39 | 6.0 | 5.9 |
| 40 | 7.6 | 6.9 |

A Deming regression analysis of the data shown in Table 15 provides a slope of 0.874 (with a 95% confidence interval of 0.820 to 0.928) and an intercept of 0.51 (with a 95% confidence interval of 0.17 to 0.85).

Example 16

Figure 18:
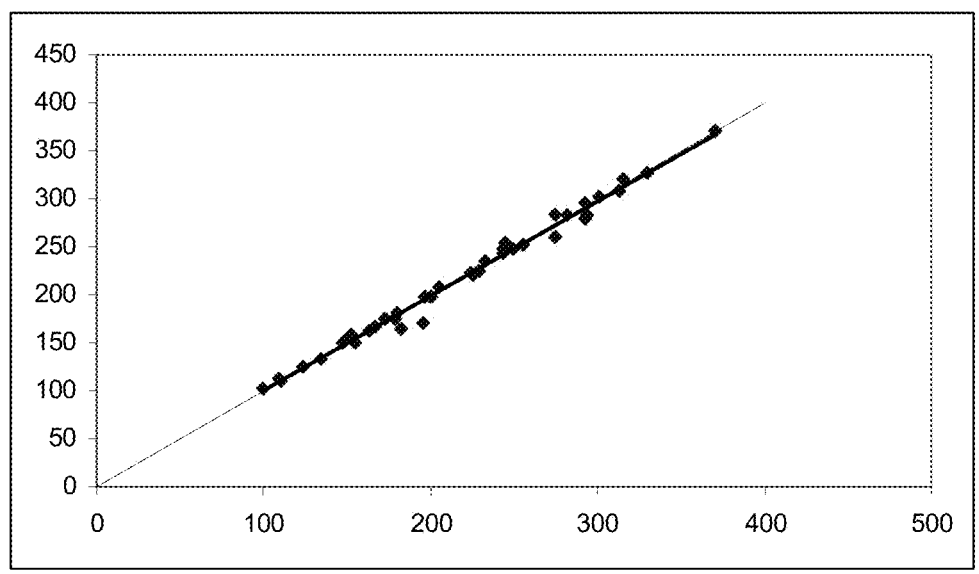
FIG. 18 is a chart showing a linear regression for correlating two separate methods for measuring transferrin.

Referring to FIG. 18, a plot of regression curve is shown for the data below in Table 16. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was transferrin.

TABLE 16

| Specimen | X | Y |
|---|---|---|
| 1 | 205 | 209.2 |
| 2 | 255 | 251.4 |
| 3 | 224 | 222.3 |
| 4 | 110 | 110.5 |
| 5 | 155 | 149.1 |
| 5 | 152 | 158.8 |
| 7 | 195 | 170.7 |
| 8 | 149 | 151.7 |

TABLE 16-continued

| Specimen | X | Y |
|---|---|---|
| 9 | 182 | 164 |
| 10 | 226 | 220.5 |
| 11 | 293 | 295 |
| 12 | 123 | 124.8 |
| 13 | 197 | 197.1 |
| 14 | 292 | 279.1 |
| 15 | 282 | 282.8 |
| 16 | 200 | 198.5 |
| 17 | 233 | 234.7 |
| 18 | 179 | 174.4 |
| 19 | 249 | 247.3 |
| 20 | 275 | 283.5 |
| 21 | 301 | 301.9 |
| 22 | 313 | 308.5 |
| 23 | 99 | 101.2 |
| 24 | 173 | 175.9 |
| 25 | 109 | 112.6 |
| 26 | 274 | 259.4 |
| 27 | 370 | 370.9 |
| 28 | 148 | 150.3 |
| 29 | 149 | 151.5 |
| 30 | 315 | 321.2 |
| 31 | 134 | 132.7 |
| 32 | 330 | 326.4 |
| 33 | 294 | 282.3 |
| 34 | 229 | 224.9 |
| 35 | 163 | 163 |
| 36 | 180 | 180.7 |
| 37 | 244 | 248 |
| 38 | 243 | 243.6 |
| 39 | 167 | 166.4 |
| 40 | 245 | 255.2 |

A Deming regression analysis of the data shown in Table 16 provides a slope of 0.997 (with a 95% confidence interval of 0.964 to 1.030) and an intercept of −0.93 (with a 95% confidence interval of −8.34 to 6.48).

Example 17

Figure 19:
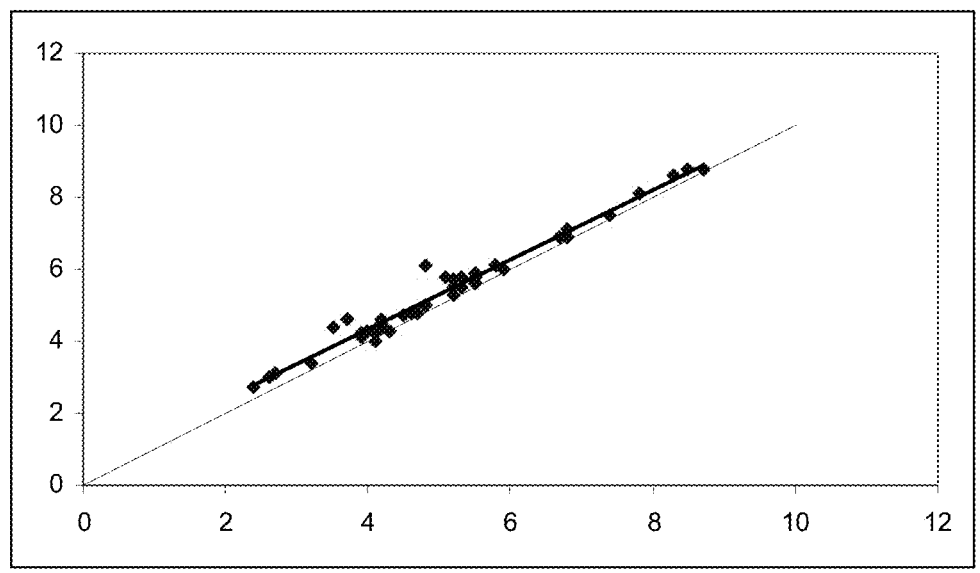
FIG. 19 is a chart showing a linear regression for correlating two separate methods for measuring uric acid.

Referring to FIG. 19, a plot of regression curve is shown for the data below in Table 17. A reference test, i.e. a "gold standard", is used to provide a reference measurement for a specimen. A second test is also performed using a different instrument and methodology to provide a second measured value. Deming regression was used to provide a linear equation that can in turn be used to calculate a reference, or normalized value, that would be obtained by using the "gold standard" from a value measured by the second methodology. In this case, the clinically significant parameter being measured was uric acid.

TABLE 17

| Specimen | X | Y |
|---|---|---|
| 1 | 4.2 | 4.5 |
| 2 | 7.8 | 8.1 |
| 3 | 4.8 | 6.1 |
| 4 | 4.5 | 4.7 |
| 5 | 2.6 | 3.0 |
| 6 | 5.2 | 5.3 |
| 7 | 3.9 | 4.1 |
| 8 | 3.7 | 4.6 |
| 9 | 4.2 | 4.4 |
| 10 | 2.4 | 2.7 |
| 11 | 4.7 | 4.8 |
| 12 | 3.9 | 4.2 |
| 13 | 5.3 | 5.5 |
| 14 | 5.9 | 6.0 |
| 15 | 3.2 | 3.4 |
| 16 | 5.2 | 5.5 |
| 17 | 5.5 | 5.8 |
| 18 | 5.3 | 5.8 |
| 19 | 5.5 | 5.9 |
| 20 | 8.7 | 8.8 |
| 21 | 8.3 | 8.6 |
| 22 | 5.5 | 5.6 |
| 23 | 3.5 | 4.4 |
| 24 | 4.8 | 5.0 |
| 25 | 7.4 | 7.5 |
| 26 | 6.8 | 6.9 |
| 27 | 4.8 | 5.0 |
| 28 | 4.3 | 4.3 |
| 29 | 6.8 | 7.1 |
| 30 | 5.2 | 5.7 |
| 31 | 6.7 | 6.9 |
| 32 | 4.0 | 4.3 |
| 33 | 5.8 | 6.1 |
| 34 | 4.2 | 4.6 |
| 35 | 4.6 | 4.8 |
| 36 | 5.1 | 5.8 |
| 37 | 2.7 | 3.1 |
| 38 | 8.5 | 8.8 |
| 39 | 4.1 | 4.2 |
| 40 | 4.1 | 4.0 |

A Deming regression analysis of the data shown in Table 17 provides a slope of 0.980 (with a 95% confidence interval of 0.937 to 1.023) and an intercept of 0.37 (with a 95% confidence interval of 0.14 to 0.60).

What is claimed is:

1. A computer-implemented method for compiling lifetime clinical data associated with an individual, the computer-implemented method comprising:
   receiving at least a first correlation factor and a second correlation factor for approximating a first value obtainable using a first test methodology based upon a second value obtainable using a second test methodology, at least one of the first correlation factor or the second correlation factor comprising a reagent lot number correlation factor correlating a reagent lot number to a standard lot number;
   receiving a measured value associated with an individual, the measured value comprising clinical data obtained using the second test methodology; and
   causing a processor to normalize the measured value using the at least the first correlation factor and the second correlation factor and store the normalized value in an electronic database, wherein the electronic database is configured to store a plurality of values associated with the individual, each one of the plurality of values normalized with respect to the first test methodology.

2. The computer-implemented method of claim 1, wherein the other of the at least one of the first correlation factor or the second correlation factor comprises an age correlation factor.

3. The computer-implemented method of claim 1, wherein the other of the at least one of the first correlation factor or the second correlation factor comprises a date range correlation factor.

4. The computer-implemented method of claim 1, further comprising storing at least one of an identification of the second test methodology, the reagent lot number, a date associated with the measured value, or an age associated with the individual, wherein the at least one of the identification of the second test methodology, the reagent lot number, the date, or the age is associated with the measured value.

5. The computer-implemented method of claim 1, wherein the first test methodology and the second test methodology are performed using different test instruments.

6. A system for compiling lifetime clinical data associated with an individual, the system comprising:
- an electronic database configured to store a plurality of values associated with an individual, each one of the plurality of values normalized with respect to a first test methodology;
- a laboratory information system configured to receive a measured value associated with the individual, the measured value comprising clinical data obtained using a second test methodology;
- a processor communicatively coupled with the laboratory information system for receiving the measured value associated with the individual; and
- a memory having computer executable instructions stored thereon, the computer executable instructions configured for execution by the processor to:
- normalize the measured value using at least a first correlation factor and a second correlation factor for approximating a first value obtainable using the first test methodology based upon a second value obtainable using the second test methodology, at least one of the first correlation factor or the second correlation factor comprising a reagent lot number correlation factor correlating a reagent lot number to a standard lot number; and
- store the normalized value in the electronic database.

7. The system of claim 6, wherein the other of the at least one of the first correlation factor or the second correlation factor comprises an age correlation factor.

8. The system of claim 6, wherein the other of the at least one of the first correlation factor or the second correlation factor comprises a date range correlation factor.

9. The system of claim 6, wherein the computer executable instructions are configured for execution by the processor to store at least one of an identification of the second test methodology, the reagent lot number, a date associated with the measured value, or an age associated with the individual, wherein the at least one of the identification of the second test methodology, the reagent lot number, the date, or the age is associated with the measured value.

10. The system of claim 6, wherein the first test methodology and the second test methodology are performed using different test instruments.

11. A non-transitory computer-readable storage medium having computer executable instructions for compiling lifetime clinical data associated with an individual, the computer executable instructions comprising:
- receiving at least a first correlation factor and a second correlation factor for approximating a first value obtainable using a first test methodology based upon a second value obtainable using a second test methodology, the first test methodology and the second test methodology performed using different instruments, at least one of the first correlation factor or the second correlation factor comprising a reagent lot number correlation factor correlating a reagent lot number to a standard lot number;
- receiving a measured value associated with an individual, the measured value comprising clinical data obtained using the second test methodology;
- normalizing the measured value using the at least the first correlation factor and the second correlation factor; and
- storing the normalized value in an electronic database configured to store a plurality of values associated with the individual, each one of the plurality of values normalized with respect to the first test methodology.

12. The non-transitory computer-readable storage medium of claim 11, wherein the other of the at least one of the first correlation factor or the second correlation factor comprises an age correlation factor.

13. The non-transitory computer-readable storage medium of claim 11, wherein the other of the at least one of the first correlation factor or the second correlation factor comprises a date range correlation factor.

14. The non-transitory computer-readable storage medium of claim 11, wherein the computer executable instructions further comprise storing at least one of an identification of the second test methodology, the reagent lot number, a date associated with the measured value, or an age associated with the individual, wherein the at least one of the identification of the second test methodology, the reagent lot number, the date, or the age is associated with the measured value.

* * * * *